United States Patent [19]

Little et al.

[11] Patent Number: 4,969,110

[45] Date of Patent: Nov. 6, 1990

[54] METHOD OF USING A PRIORI INFORMATION IN COMPUTERIZED TOMOGRAPHY

[75] Inventors: Francis H. Little; David L. Hampson, both of Cincinnati, Ohio

[73] Assignee: General Electric Company, Cincinnati, Ohio

[21] Appl. No.: 226,497

[22] Filed: Aug. 1, 1988

[51] Int. Cl.$^5$ ..................... G06F 15/20; G01N 23/04
[52] U.S. Cl. .................... 364/550; 364/560; 364/413.21; 358/96; 378/21; 378/901
[58] Field of Search .......... 364/550, 560, 564, 413.19, 364/413.21, 413.14, 413.15; 358/101, 106, 107, 111, 96; 250/491.1, 359.1; 378/21, 54, 23, 56, 4, 901, 58

[56] References Cited

U.S. PATENT DOCUMENTS

| | | | |
|---|---|---|---|
| 4,303,829 | 12/1981 | Wagner | 250/455 T |
| 4,375,696 | 3/1983 | Wagner | 378/20 |
| 4,384,209 | 5/1983 | Wagner et al. | 378/14 |
| 4,506,327 | 3/1985 | Tam | 364/414 |
| 4,582,993 | 4/1986 | Bhattacharya et al. | 250/359.1 |
| 4,672,650 | 6/1987 | Masanobu | 378/4 |

FOREIGN PATENT DOCUMENTS 2192120  12/1987  United Kingdom .

Primary Examiner—Parshotam S. Lall
Assistant Examiner—Ellis B. Ramirez
Attorney, Agent, or Firm—Jerome C. Squillaro

[57] ABSTRACT

To improve computerized tomography (CT) imaging quality, a priori information of the test object is developed by probing the surfaces thereof at a multiplicity of points sufficient to spatially locate and define the envelope of the test object cross section to be imaged. A CT scan of the test object is then performed, and the CT image reconstructed therefrom is corrected with this a priori information. To expedite a priori information development, the convex hull of the test object is constructed from X-ray projection data and fitted with the probe developed measurement data to define the cross section envelope.

9 Claims, 2 Drawing Sheets

METHOD OF USING A PRIORI INFORMATION IN COMPUTERIZED TOMOGRAPHY

BACKGROUND OF THE INVENTION

The present invention relates to industrial computerized tomography (ICT) and particularly to the construction of two-dimensional, cross sectional, computerized tomography (CT) images of objects with the aid of a priori information regarding the objects.

ICT inspection of industrial products is a powerful quality assurance tool for determining if the internal characteristics of the manufactured products are in accordance with design specifications and for detecting any internal flaws. For example, in the manufacture of gas turbine engines, there are certain critical parts, such as turbine blades that are intricately cast with internal passages, whose internal characteristics are of paramount importance if safe, long term engine Performance is to be achieved. The passage walls must be of design thickness and the existence of internal flaws, such as cracks, voids, microshirks, porosities, coldshuts, passage blockages, etc., must be within design tolerances if the part is to withstand the rigors of an engine operating environment.

To perform an ICT inspection, the part is positioned between an X-ray source and a detector typically consisting of an array of detector elements aligned with a highly collimated, fan-shaped beam of X-rays projected by the source at a transverse slice of the part. The part is rotated in steps through an angle of at least 180° plus the fan beam included angle, if possible, and the part slice is irradiated from a multiplicity of different projection angles. The attenuation of the X-ray flux is detected by each detector at each projection angle, and a computer reconstructs an image of the slice cross section from the X-ray attenuation signals generated by the detector elements at each projection angle. For certain part geometries, the X-ray path length through certain slices thereof can be so great at some projection angles that X-ray penetration is insufficient to generate meaningful attenuation data. In other cases, certain projection angles may be obstructed by the presence of associated objects. Obviously, the inability of obtaining meaningful X-ray attenuation data throughout the complete scanning range degrades the quality of the reconstructed slice cross section image. The image is marred by artifacts, and the internal characteristics of the part become ill-defined and blurred to the point that internal flaws become difficult to detect.

To improve CT image quality, resort to a priori or known information about the object under inspection has been proposed. In the commonly assigned application of K. C. Tam entitled "Method to Obtain Object Boundary Information in Limited-Angle Computerized Tomography", Ser. No. 032,804, filed Apr. 1, 1987, now U.S. Pat. No. 4,888,693 the disclosure of which is specifically incorporated herein by reference, the exterior boundary of the test object is estimated. This is accomplished by performing a low energy X-ray exposure of the test object at each CT projection or scanning angle to determine the object edges in each instance. The low energy X-ray data generated by the detector elements are computer processed as a succession of curve fittings at the object edges to construct a polygon-shaped region approximating the convex hull of the object. If the object is basically convex in shape, such as cylindrical, the convex hull corresponds quite closely to the object boundary. This convex hull information is then used to correct the CT image reconstruction process by setting to zero those pixels known to be beyond the object boundary, thereby achieving a high quality image of the slice cross section.

Unfortunately, not all test objects are convex in shape. Many have significantly concave boundary features. Consequently, the convex hull then becomes merely an approximation of the object boundary, which diminishes in value as the degree and number of concave boundary features increases.

It is accordingly an object of the present invention to provide a method for improving the quality of CT image reconstruction.

A further object is to provide a method of the above-character, wherein more precise a priori information regarding the test object is utilized in CT image reconstruction.

An addition object is to provide a method of the above-character, wherein physical measurements of the test object boundary are utilized as a priori information in the reconstruction of CT images.

Other objects of the invention will in part be obvious and in part appear hereinafter.

SUMMARY OF THE INVENTION

In accordance with the present invention, there is provided an improved method for reconstructing computerized tomography (CT) images using predetermined a priori or known information regarding the test object's boundary geometry. To this end, prior to performing a CT scan at a multiplicity of X-ray projection angles, the exterior boundary of the object, as fixed in its test position, is physically probed at a multiplicity of surface or boundary points according to a predetermined mapping plan to measure the object contour and thus locate the probed boundary points on an X-Y coordinate system. The resulting probed boundary point measurement data are computer processed to generate boundary data defining the envelope of the test object cross section. The test object is then subjected to a normal CT scan at a multiplicity of X-ray projection angles, and an image of the projected slice cross section is reconstructed in a conventional manner, such as by filtered backprojection. The reconstructed X-ray image is then processed in an iterative manner involving repeated transformations between object space and projection space and correcting the reconstructed image in object space by resetting to zero those pixels known from the generated boundary data to lie beyond the object cross section envelope. The display of the corrected, reconstructed CT image is of superior quality, thereby facilitating the inspection and measurement of the test object's internal characteristics and the detection and measurement of internal flaws.

To expedite the test object boundary probing step, the present invention further includes the steps of constructing the convex hull of the test object, probing several boundary reference points on those convex surface formations of the test object which are accurately defined by the convex hull, and fitting the constructed convex hull to these probed convex surface boundary points. The envelope-defining boundary data for the test object is then generated using the constructed convex hull data for the convex surface formations and the probed boundary point data for the concave surface formations thereof.

The invention accordingly comprises a series of method steps which will be exemplified in the detailed description hereinafter set forth, and the scope of the invention will be indicated in the claims.

For a fuller understanding of the nature and objects of the invention, reference may be had to the following description taken in connection with the accompanying drawings, in which.

DETAILED DESCRIPTION

Figure 1:
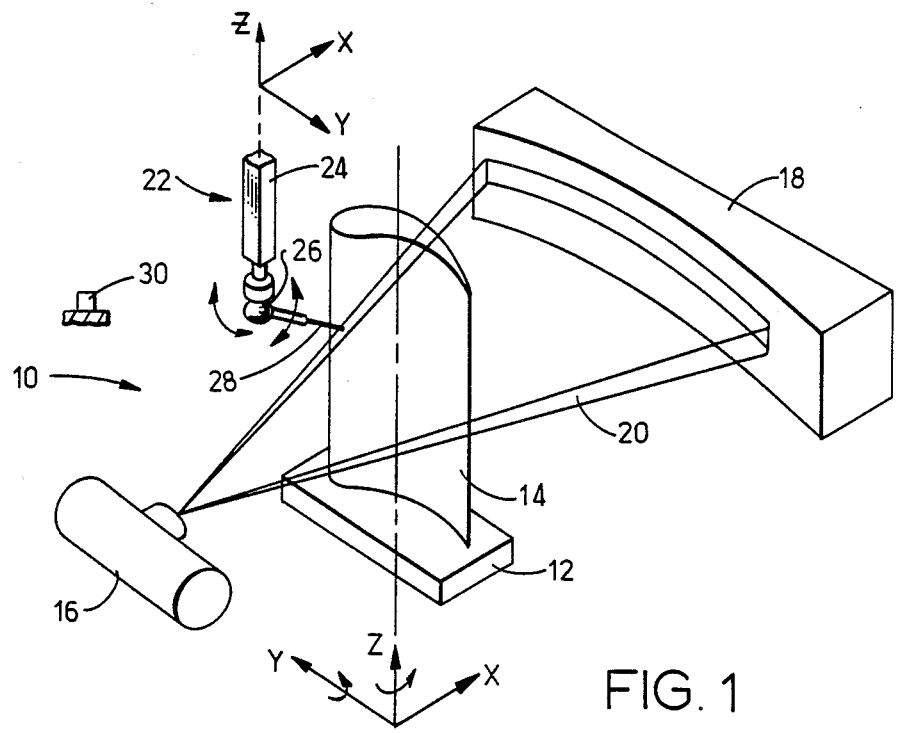
FIG. 1 is a simplified, perspective view of an industrial computerized tomography (CT) inspection station utilized in the method of the present invention.

An industrial computerized tomography (ICT) inspection station, generally indicated at 10 in FIG. 1, includes a manipulator support 12 fixedly mounting an object 14 to be inspected. In conventional fashion, the manipulator support is capable of linear movement along horizontal X and Y orthogonal axes and a vertical Z axis, as well as rotational motion about the Z axis and at least one of the X and Y axes, typically the latter. These controlled manipulator support movements variously position and orient the test object between an X-ray source 16 and a typically horizontal array 18 of detector elements. The source projects a collimated, fan-shaped beam 20 of X-rays at a thin slice of the test object cross section, and the differentially attenuated X-ray flux is sensed by the individual detectors of array 18.

As a signal feature of the present invention, the inspection station also includes a measurement inspection system, generally indicated at 22. This system includes a depending support 24 mounting a motorized probe head 26 from which projects a touch probe stylus 28. The support is mounted for controlled linear movement along orthogonal X, Y and Z axes, while the probe head is rotatable about orthogonal axes to properly orient the stylus with respect to the test object. An appropriate measurement inspection system for use in the present invention is the PH9 Automated Inspection System marketed by Renishaw Inc. of Schaumburg, Ill. It will be appreciated that, rather than a touch probe, the measurement inspection system may utilize a noncontacting probe, such as a laser scanning probe also available from Renishaw Inc.

The measurement inspection system, after having been calibrated by probing a fixed reference point 30, manipulates stylus 28 to probe the test object exterior or boundary surface at a multiplicity of points in accordance with a programmed mapping plan and thus locate the probed surface points in space on the basis of the same three-axes coordinate system that test object 14 is positioned by support manipulator 12. Thus, probe and manipulator support movements and positionings may be controlled by a common computer numerical controller (CNC), not shown.

To perform an inspection, test object 14 is typically first scanned in a digital radiographic (DR) mode wherein the test object is indexed vertically along the Z axis through X-ray fan beam 20 by manipulator support 12 to generate a succession of radiographs of the object cross section. If, from these radiographs, the operator observes a suspect area of the test object, one or more computer tomography (CT) slices involving the suspect area are selected for ICT inspection. As is well known, ICT inspection involves vertically positioning the test object along the Z axis to align a selected slice plane of the suspect area with the X-ray fan beam and then rotating the test object through an angle of at least 180° plus the X-ray fan beam included angle in a series of equal steps. At each step or projection angle of the CT scan, the attenuation of the X-ray flux by the test object density included in the CT slice is sensed by the individual detectors of array 18 to generate X-ray attenuation data. This data is processed over the complete CT scanning angle in a conventional fashion, such as by filtered back-projection, to reconstruct a CT image of the test object cross section included in the CT slice.

Figure 3:
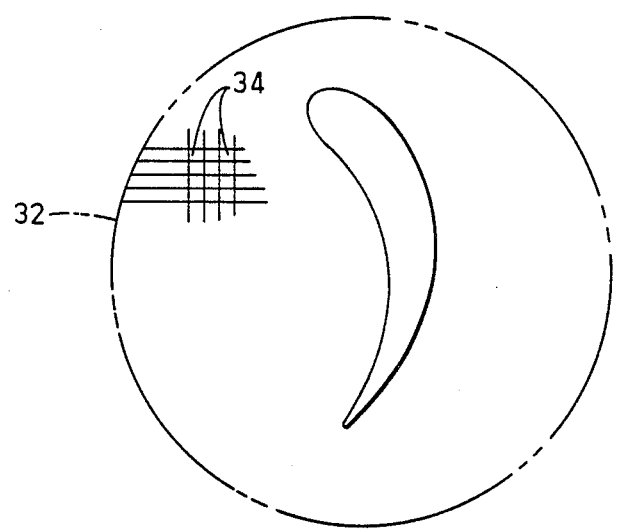
FIG. 3 illustrates the CT image of a cross sectional slice of the test object reconstructed solely from X-ray attenuation data.

FIG. 3 shows a typical display 32 on which the slice cross section image, as reconstructed solely from X-ray attenuation data, is displayed. This display is comprised of a matrix of pixels 34. When reconstructing a CT image, the position of the test object in the display field of view at each projection angle of the CT scan is unknown. Thus, the degree of X-ray flux attenuation sensed by each detector element at a particular projection angle must be averaged over those pixels of the display which are effectively aligned between it and the X-ray source. As can be appreciated from FIG. 3, a vast majority of these pixels are beyond the test object cross section envelope, and yet they are proportionally activated from the X-ray attenuation data as though they were involved within the test object cross section envelope. It is only after the X-ray data from all the detectors at all of the projection angles throughout the complete CT scanning angle are processed together that a CT image of the test object slice cross section can be reconstructed with reasonable boundary definition.

Figure 2:
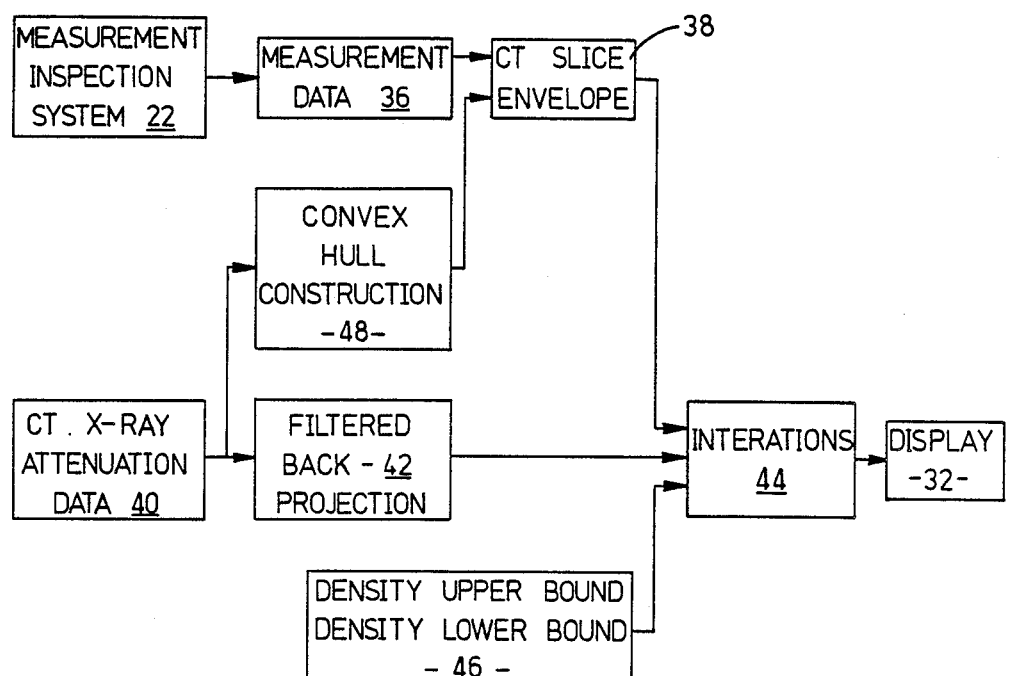
FIG. 2 is a functional block diagram depicting the various steps of processing the data obtained from the inspection station of FIG. 1.
Figure 5:
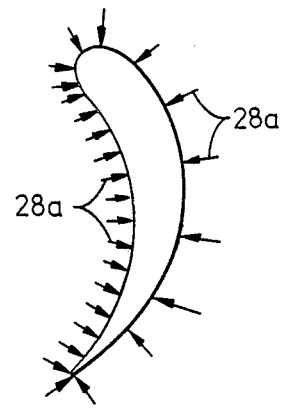
FIG. 5 illustrates the test object slice cross section envelope generated in part from the convex hull construction and in part from probed measurement data.

In accordance with the present invention, test object measurement data developed by measurement inspection system 22 is processed with the CT X-ray attenuation data, as illustrated in the functional block diagram of FIG. 2, to reconstruct a test object slice cross section image of improved quality. Thus, prior to conducting a CT inspection of one or more slice planes through a suspect area of the test object as identified during DR inspection, the measurement inspection system 22 is activated to conduct a succession of probings of the test object surfaces bounding the slice in accordance with a programmed mapping plan. These probings, indicated at 28a in FIG. 5, precisely locate the probed boundary points of the test object in space relative to the same X-Y coordinate system applied in the processing and display of the reconstructed CT image (FIG. 3). The number of probings and separations between probed boundary points are predetermined based on the particularly geometry of the test object surface contour involved in order to generate sufficient a priori measurement data (block 36) to faithfully reproduce the external boundary or envelope (block 38) of the test object slice to be CT inspected.

Once the slice envelope is determined and referenced to the appropriate X-Y coordinate system, a CT inspection of the suspect test object slice or slices is conducted to generate X-ray attenuation data (block 40) from which a CT image of the object slice cross section is reconstructed by suitable means, such as filtered backprojection indicated by block 42 in FIG. 2. The reconstructed CT image is transformed in an iterative process (block 44) back and forth between object space and projection space, with each transformation to object space being corrected by the a priori CT slice envelope data. Basically, this involves limiting the application or allotment of the X-ray attenuation data only to those pixels 34 (FIG. 3) involved in the display of the cross section image. This has the effect of setting to zero those pixels shown to be located beyond the test object boundary by the envelope-defining boundary data.

As taught in the above-noted Tam U.S. Pat. No. 4,888,693 and Tam U.S. Pat. No. 4,506,327, other available a priori information regarding the test object are the upper and lower bounds of its material density, block 46 in FIG. 2. Thus, with the iterations process 44, additional corrections may be made by resetting to the upper bound those pixels 34 manifesting an object density in excess of the upper bound and resetting to zero those pixels manifesting an object density less than the lower bound.

If a complete CT scanning angle is obstructed or the X-ray flux is seriously over-attenuated at certain projection angles, then the limited angle image reconstruction algorithm developed in the article "Tomographical Imaging with Limited-Angle Input", Tam and Perez-Mendez, J. Opt. Soc. Am., 71 (1981) pages 582–592, may also be utilized in iterations process 44. The result is a corrected, reconstructed CT image of the object slice cross section, which is displayed on display 32 with vastly improved definition. Thus, even small flaws can be readily visualized, and internal features are displayed with such clarity that their dimensional characteristics can be accurately guaged.

Figure 4:
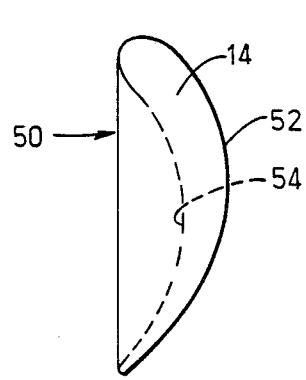
FIG. 4 illustrates a convex hull construction for the test object slice cross section.

In accordance with an additional feature of the present invention, to expedite development of the measurement data 36 by measurement inspection system 22, the convex hull of the test object at the CT slice planes is generated (block 48) from X-ray projection data. As disclosed in the above-cited Tam U.S. Pat. No. 4,888,693 the test object is scanned by the fan beam 20 of X-rays of an energy level lower than the normal CT scanning level at a multiplicity of projection angles over the full CT scanning angle. The detected X-ray data are projected for each projection angle, and the projections backprojected to yield backprojection strips, each with the object boundary clearly demarcated. All of the backprojection strips are overlapped, either by intersection or superimposition, to construct a polygon shaped region corresponding to the convex hull of the test object, as indicated at 50 in FIG. 4. It is seen that this convex hull construction conforms quite exactly to the convex surface formation 52 of the object cross section envelope, but departs significantly from the concave surface formation 54 thereof. This indicates that the CT slice envelope boundary data 38 can be generated using the convex hull construction to define the convex surface portions thereof and the measurement inspection system probings to define the concave surface portions. This is illustrated in FIG. 2, wherein the convex hull data 48 and the probed measurement data 36 are processed in combination to generate the CT slice envelope 38. Since the convex hull data can precisely define and locate the object's convex surface formation, only a representative small number of probings thereof by the measurement inspection system are required to reference the boundary point data generated by the more concentrated and numerous probings of the concave surface formations to the convex hull data. Since the convex hull data can be generated considerably more expeditiously than the probed boundary point measurement data, considerable time is saved in developing the CT slice envelope and thus the ultimate reconstruction of the a priori information-corrected, high quality CT image as displayed by display 32.

From the foregoing description, it is seen that the present invention affords significant improvements in CT imaging to greatly facilitate industrial nondestructive inspection of critical parts, which, by necessity, is becoming increasingly more prevalent in a number of industries. Thus, it is submitted that the objects set forth above, including those made apparent from the preceding description, are efficiently attained, and, since certain changes may be made in the disclosed method and the various steps thereof without departing from the scope of the invention, it is intended that all matters contained herein be interpreted as illustrative and not in a limiting sense.

Having described the invention, what is claimed as new and desired to secure by Letters Patent is:

1. A method of reconstructing a computerized tomography (CT) image of a test object cross section comprising the steps of:
   A. supporting the test object in a test position;
   B. probing the test object at a multiplicity of exterior surface points in accordance with a predetermined mapping plan;
   C. developing measurement data locating the probed surface points in space;
   D. generating from the measurement data envelope boundary data defining the envelope of the test object cross section to be imaged;
   E. exposing the test object to X-rays at a multiplicity of projection angles to generate X-ray attenuation data at each projection angle;
   F. processing said X-ray attenuation data to reconstruct a CT image of the test object cross section;
   G. correcting the reconstructed image with said boundary data by limiting the application of said X-ray attenuation data to the test object cross section; and
   H. displaying a corrected, reconstructed image of the test object cross section.

2. The method defined in claim 1, wherein said corrected, reconstructed image is displayed on a pixel matrix display, said correcting step includes setting to zero said X-ray attenuation data allotted to those display pixels indicated by said boundary data to lie beyond the imaged cross section envelope of the test object.

3. The method defined in claim 2, wherein said correcting step further includes resetting those pixels displaying the cross section image to the known density bounds of the test object.

4. The method defined in claim 2, which further includes the steps of developing X-ray projection data defining the convex hull of the test object cross section, and selectively combining said X-ray projection data and said measurement data to generate said envelope defining boundary data.

5. The method defined in claim 2, wherein said correcting step includes iteratively transforming said reconstructed CT image back and forth between object space and projection space, and correcting each image transformation to object space with said boundary data.

6. A method of reconstructing a computerized tomography (CT) image of the cross section of a test object for portrayal on a pixel matrix display, said method comprising the steps of:

A. supporting the test object in a test position;

B. probing the concave exterior surface formations of the test object at a multiplicity of points to generate measurement data locating the probed concave surface points in space;

C. scanning the test object at a multiplicity of projection angles to generate X-ray projection data at each projection angle defining the convex hull of the test object and to locate in space the convex surface formations of the test object;

D. fitting said measurement data and X-ray projection data together to generate boundary data defining and locating in space the complete envelope of the test object cross section;

E. exposing the test object to X-rays at a multiplicity of projection angles to generate X-ray attenuation data indicative of the density of the test object cross section at each projection angle;

F. processing said X-ray attenuation data to reconstruct a CT image of the test object cross section;

G. correcting said CT image with said boundary data by resetting to zero those display pixels located beyond said test object cross section envelope; and H. displaying a corrected, reconstructed CT image of the test object cross section on said pixel matrix display.

7. The method defined in claim 6, wherein said probing step further includes probing said convex surface formations of the test object at a sufficient member of points to generate reference measurement data, and said fitting step uses said reference measurement data to spatially relate said X-ray projection data to said concave surface formation measurement data in generating said envelope-defining boundary data of the test object cross section.

8. The method defined in claim 7, wherein said correcting step further includes resetting those pixels displaying the cross section image to the known density bounds of the test object.

9. The method defined in claim 8, wherein said correcting step includes iteratively transforming said reconstructed CT image back and forth between object space and projection space, and correcting each transformation to object space with said boundary data and the density bounds of the test object.

* * * * *